US00PP30658P2

(12) United States Plant Patent
Kievit

(10) Patent No.: US PP30,658 P2
(45) Date of Patent: Jul. 2, 2019

(54) ***SALVIA* PLANT NAMED 'SKY BLUE MARVEL'**

(50) Latin Name: *Salvia nemorosa*
Varietal Denomination: Sky Blue Marvel

(71) Applicant: Ball Horticultural Company, West Chicago, IL (US)

(72) Inventor: Christa Kievit, Hem (NL)

(73) Assignee: Ball Horticultural Company, West Chicago, IL (US)

( * ) Notice: Subject to any disclaimer, the term of this patent is extended or adjusted under 35 U.S.C. 154(b) by 0 days.

(21) Appl. No.: 15/999,953

(22) Filed: Sep. 4, 2018

(51) Int. Cl.
*A01H 5/02* (2018.01)
*A01H 6/50* (2018.01)

(52) U.S. Cl.
USPC ..... Plt./475

(58) Field of Classification Search
USPC ..... Plt./263.1, 475
See application file for complete search history.

*Primary Examiner* — Susan McCormick Ewoldt
*Assistant Examiner* — Karen M Redden
(74) *Attorney, Agent, or Firm* — Audrey Charles

(57) ABSTRACT

A new and distinct cultivar of *Salvia* plant named 'Sky Blue Marvel', characterized by its light violet-blue colored flowers, medium green-colored foliage, and moderately vigorous, upright-mounded growth habit, is disclosed.

2 Drawing Sheets

Latin name of genus and species of plant claimed: *Salvia nemorosa.*

Variety denomination: 'Sky Blue Marvel'.

BACKGROUND OF THE INVENTION

The present invention relates to a new and distinct cultivar of *Salvia* plant botanically known as *Salvia nemorosa* and hereinafter referred to by the cultivar name 'Sky Blue Marvel'.

The new cultivar originated in a controlled breeding program in Hem, The Netherlands during August 2010. The objective of the breeding program was the development of *Salvia* cultivars having large flowers and compact growth habits.

The new *Salvia* cultivar was the result of open-pollination within an insect-cage environment of three proprietary *Salvia nemorosa* breeding selections coded JO81-1, JO81-2, and JO81-3, not patented, characterized by light violet-blue colored flowers, medium green-colored foliage, and moderately vigorous, semi-upright growth habit. The new cultivar was discovered and selected as a single flowering plant within the progeny of the above stated open-pollination during July 2012 in a controlled environment in Hem, The Netherlands.

Asexual reproduction of the new cultivar by terminal stem cuttings since July 2012 in Hem, The Netherlands and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Sky Blue Marvel' as a new and distinct cultivar of *Salvia* plant:

1. Light violet-blue colored flowers;

2. Medium green-colored foliage; and
3. Moderately vigorous, upright-mounded growth habit.

Plants of the new cultivar differ from plants of the parents primarily in having a lighter shade flower color, and longer inflorescences.

Of the many commercially available *Salvia* cultivars, the most similar in comparison to the new cultivar is 'Blue Marvel', U.S. Plant Pat. No. 27,018. However, in side by side comparisons, plants of the new cultivar differ from plants of 'Blue Marvel' in at least the following characteristics:

1. Plants of the new cultivar have a flower color that is lighter than plants of 'Blue Marvel';
2. Plants of the new cultivar have larger sized corollas than plants of 'Blue Marvel'; and
3. Plants of the new cultivar have larger sized leaves than plants of 'Blue Marvel'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Sky Blue Marvel'. The plants were approximately four months old. The plants were grown in one-gallon containers for approximately 12 weeks in a greenhouse in Elburn, Ill. Plants were given two pinches, one at one week before transplant and one two weeks after transplant.

DETAILED BOTANICAL DESCRIPTION

Figure 1:
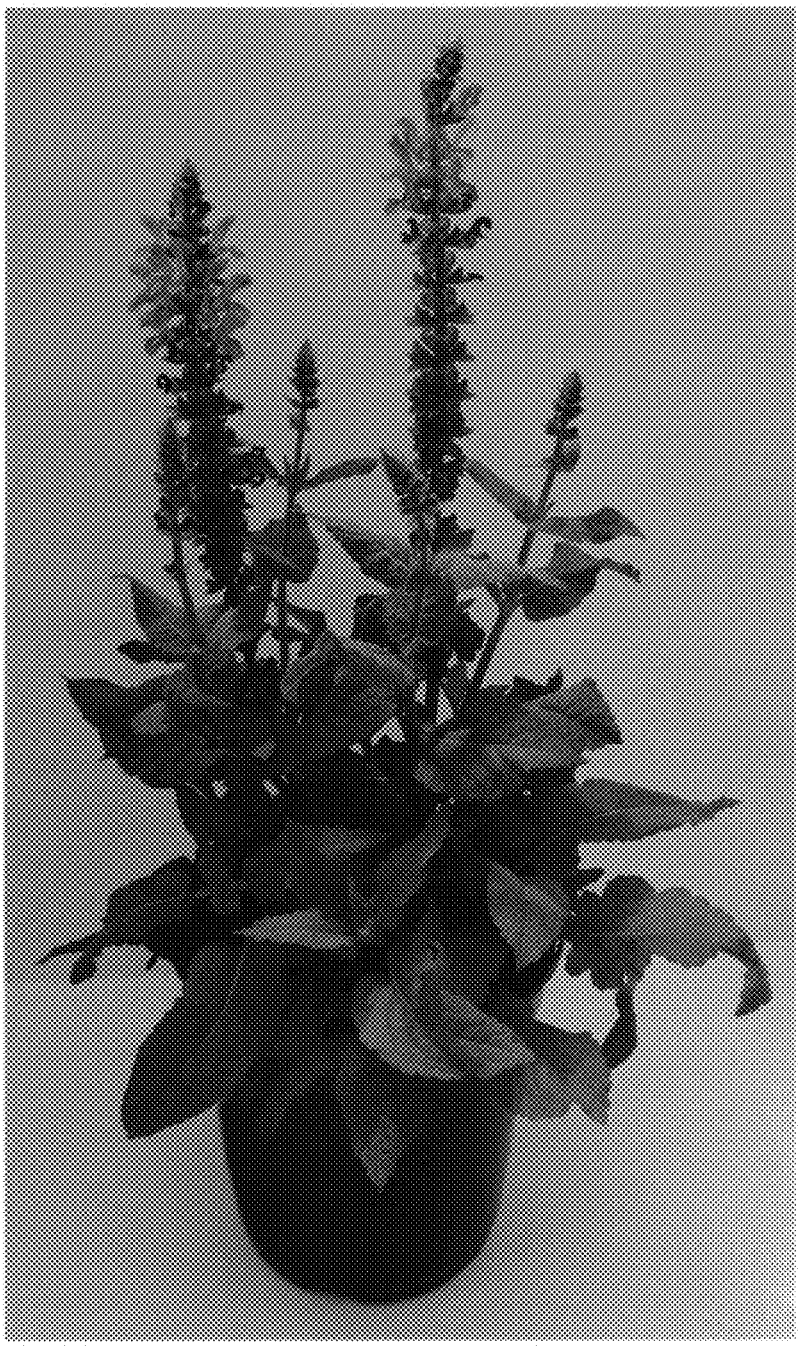
FIG. 1 illustrates a side view of the overall growth and flowering habit of 'Sky Blue Marvel'.
Figure 2:
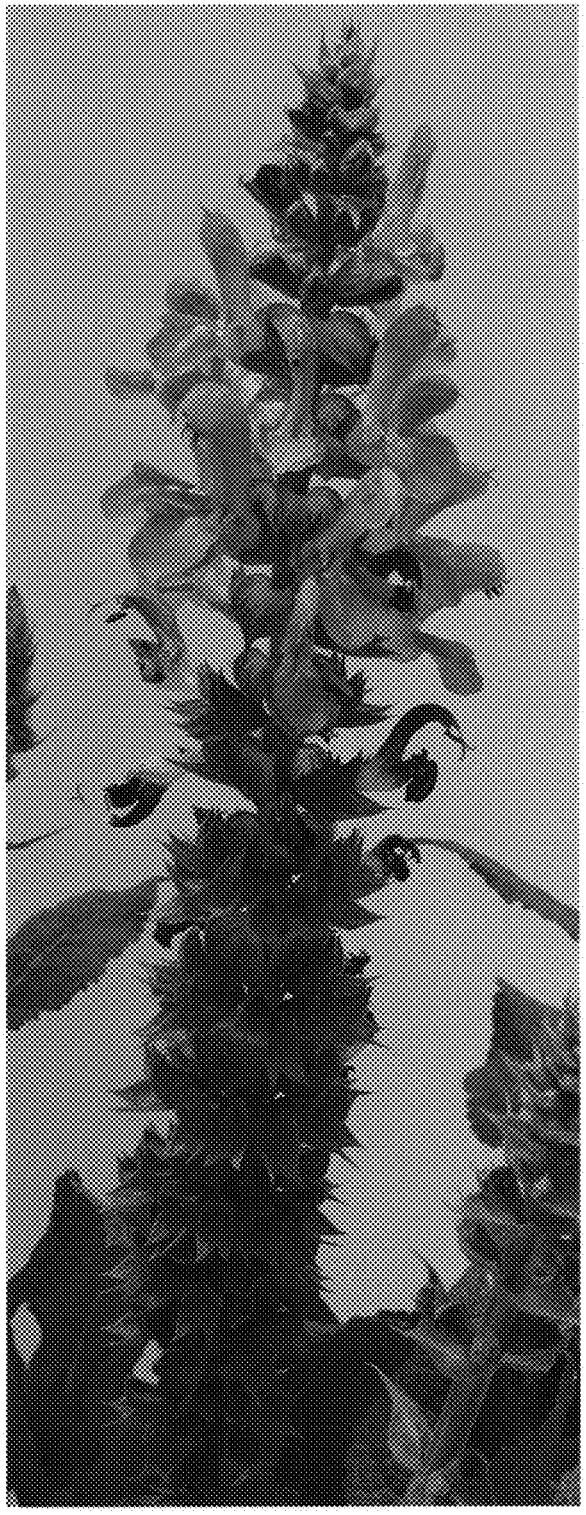
FIG. 2 illustrates a close-up view of an individual inflorescence of 'Sky Blue Marvel'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in July 2018 under natural light conditions in West Chicago, Ill.

The following descriptions and measurements describe approximately four-month old plants produced from cuttings from stock plants and grown under conditions comparable to those used in commercial practice. The plants were grown in one-gallon containers for approximately 12 weeks in a greenhouse in Elburn, Ill. Plants were given two pinches, one at one week before transplant and one two weeks after transplant. Greenhouse temperatures were maintained at approximately 65° F. to 70° F. (18.3° C. to 21.1° C.) during the day and approximately 55° F. to 60° F. (12.8° C. to 15.6° C.) during the night. No supplemental lighting was provided. Measurements and numerical values represent averages of typical plants.

Botanical classification: *Salvia nemorosa* 'Sky Blue Marvel'.

Parentage:

*Female and male parents*.—Three proprietary *Salvia nemorosa* breeding selections coded JO81-1, JO81-2, and JO81-3, not patented.

Propagation:

*Type cutting*.—Terminal stem.

*Time to initiate roots*.—Approximately 12 to 15 days.

*Time to produce a rooted cutting*.—Approximately 35 to 42 days.

*Root description*.—Fine, fibrous.

*Rooting habit*.—Freely branching.

Plant description:

*Commercial crop time*.—Approximately 10 to 12 weeks from a rooted cutting to finish in a 15 cm pot.

*Growth habit and general appearance*.—Herbaceous perennial, moderately vigorous, upright-mounded growth habit.

*Hardiness*.—USDA Zone 4a (−30° F. to −25° F./−34.4° C. to −31.7° C.).

*Size*.—Height from soil level to top of plant plane: Approximately 38.0 cm. Width: Approximately 36.0 cm.

*Branching habit*.—Freely branching. Pinching enhances lateral branching. Quantity of branches per plant: Approximately 7.

*Branch*.—Shape: Square in cross section. Strength: Strong. Length to base of inflorescence: Approximately 18.0 cm. Diameter: Approximately 5.0 mm. Length of central internode: Approximately 4.5 cm. Texture: Densely pubescent. Color of young stems: 146D. Color of mature stems: 146B tinted with 187A in sun.

*General description*.—Quantity of leaves per main branch: Approximately 6. Fragrance: Strong, sage-like. Form: Simple. Arrangement: Opposite.

*Leaves*.—Aspect: Acute to perpendicular angle to stem. Shape: Lanceolate. Margin: Crenate. Apex: Acute. Base: Cordate. Venation pattern: Pinnate. Length of mature leaf: Approximately 12.0 cm. Width of mature leaf: Approximately 4.5 cm. Texture of upper surface: Rugose, sparsely pubescent with very short hairs. Texture of lower surface: Rugose, densely pubescent with very short hairs. Color of upper surface of young and mature foliage: Closest to 137A with venation of 145D. Color of lower surface of mature foliage: Closest to 137C with venation of 147D.

*Petiole*.—Length: Approximately 3.0 cm. Diameter: Approximately 4.0 mm. Texture: Densely pubescent. Color: Closest to 147D.

Flowering description:

*Flowering habit*.—'Sky Blue Marvel' is freely flowering under outdoor growing conditions with substantially continuous blooming from early spring through late summer and with limited flowering under short winter days in a greenhouse environment.

*Lastingness of individual floret*.—Approximately 4 to 5 days.

Inflorescence description:

*General description*.—Type: Spikes in verticillaster arrangement, florets in clusters of two to three, not persistent. Quantity of inflorescences per plant: Approximately 4. Fragrance: Faint, sweet. Length or height of inflorescence: Approximately 5.0 cm to 14.0 cm. Width of inflorescence: Approximately 3.5 cm to 4.5 cm. Quantity of fully-open flowers per inflorescence: Approximately 20 with up to 40 at peak flowering.

*Peduncle*.—Shape: Square in cross section. Strength: Strong. Aspect: Erect. Length: Approximately 2.5 cm to 3.0 cm. Diameter: Approximately 2.0 mm to 4.0 mm. Texture: Densely pubescent. Color: 146B tinted with 187A in sun.

Flower description:

*Type*.—Single, zygomorphic.

*Bud*.—Rate of opening: Generally takes 2 to 3 days for bud to progress from first color to fully open flower.

*Bud just before opening*.—Shape: Obovoid. Length: Approximately 7.0 mm. Diameter: Approximately 4.0 mm. Texture: Densely pubescent. Color: Calyx of 146C to 146D with a faint overlay of 187A on tips and margins; petal portion of N89A.

*Corolla*.—Shape: Bilabiate, lower lip having three lobes, base fused. Width: Approximately 9.0 mm. Length: Approximately 1.5 cm. Depth: Approximately 1.9 cm.

*Upper lip*.—Shape: Hooded. Margin: Entire. Apex: Rounded. Length from throat: Approximately 1.0 cm. Width: Approximately 1.0 mm. Texture of inner surface: Glabrous. Texture of outer surface: Sparsely pubescent. Color of inner surface when first and fully open: 92B. Color of outer surface when first and fully open: 91A to 91B.

*Lower lip*.—Shape of central lobe: Orbicular, cupped. Shape of lateral lobes: Oblong. Margin: Entire, central lobe wavy. Apex of central lobe: Emarginate. Apex of lateral lobes: Rounded. Length from throat of central lobe: Approximately 7.0 mm. Width of central lobe: Approximately 9.0 mm. Length from throat of lateral lobes: Approximately 5.0 mm. Width of lateral lobes: Approximately 2.0 mm. Texture of upper surface: Glabrous. Texture of lower surface: Sparsely pubescent. Color of upper surface when first and fully open: Lateral lobes of 93B to 93C, central lobe 91A. Color of lower surface when first and fully open: Lateral lobes of 93C, central lobe 93C to 93D.

*Corolla tube*.—Length: Approximately 7.0 mm. Diameter at opening: Approximately 4.0 mm. Diameter at base: Approximately 2.0 mm. Texture of inner and outer surfaces: Glabrous. Color of inner surface when first and fully open: NN155D. Color of outer surface when first and fully open: NN155D tinted with 93D at distal end.

*Calyx*.—Shape: Cupped. Length: Approximately 7.0 mm. Diameter: Approximately 5.0 mm.

*Sepals*.—Quantity per flower: 5, fused. Shape: Ovate. Apex: Acute. Length: Approximately 7.0 mm. Width of lobes: Approximately 2.0 mm to 4.0 mm. Texture of inner and outer surfaces: Densely pubescent. Color of inner surface: 146D. Color of outer surface: 146C to 146D.

*Bracts*.—Quantity: One bract located at the base of floret cluster. Shape: Ovate. Apex: Acuminate. Texture of inner (upper) surface: Glabrous. Texture of outer (lower) surface: Densely pubescent. Color of inner and outer surfaces: 137B with 146D.

*Pedicel*.—Strength: Strong, flexible. Aspect: At an acute angle. Length: Approximately 2.0 mm. Diameter: Less than 1.0 mm. Texture: Densely pubescent. Color: 146D tinted with 187A.

*Reproductive organs*.—Androecium: Stamen quantity: 2 per flower, dorsifixed, strongly curved. Stamen length: Approximately 1.7 cm. Filament length: Approximately 1.5 cm. Filament color: NN155D with a faint overlay of 90A at base. Anther shape: Oblong. Anther length: Approximately 2.0 mm. Anther color: N92A with 103A. Pollen amount: Not observed. Gynoecium: Pistil quantity: 1 per flower, slightly curved. Pistil length: Approximately 1.8 cm. Stigma shape: Cleft, two-parted. Stigma length: 2.0 mm. Stigma color: 90A. Style length: Approximately 1.4 cm. Style color: NN155D. Ovary length: Approximately 2.0 mm. Ovary color: 144C with N25A.

Seed and fruit production: Neither seed nor fruit production has been observed.

Disease and pest resistance: Resistance to pathogens and pests common to *Salvia* has not been observed.

What is claimed is:

1. A new and distinct cultivar of *Salvia* plant named 'Sky Blue Marvel', substantially as herein illustrated and described.

* * * * *